(12) United States Patent
Lesser et al.

(10) Patent No.: US 7,228,171 B2
(45) Date of Patent: Jun. 5, 2007

(54) SIGNAL ANALYSIS, HEAT FLOW MANAGEMENT, AND STIMULATION TECHNIQUES TO TREAT MEDICAL DISORDERS

(75) Inventors: Ronald P. Lesser, Baltimore, MD (US); W. Robert S. Webber, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 499 days.

(21) Appl. No.: 10/413,520

(22) Filed: Apr. 15, 2003

(65) Prior Publication Data

US 2003/0171685 A1 Sep. 11, 2003

Related U.S. Application Data

(63) Continuation-in-part of application No. 09/691,051, filed on Oct. 19, 2000, now Pat. No. 6,882,881.

(60) Provisional application No. 60/201,188, filed on May 2, 2000, provisional application No. 60/160,328, filed on Oct. 19, 1999.

(51) Int. Cl.
*A61N 1/37* (2006.01)

(52) U.S. Cl. .......................................................... 607/3

(58) Field of Classification Search ................ 600/373, 600/377, 378, 544, 545; 607/2, 3, 45, 46, 607/96, 110, 113, 118
See application file for complete search history.

(56) References Cited

U.S. PATENT DOCUMENTS

| | | | |
|---|---|---|---|
| 3,170,465 A | 2/1965 | Henney | |
| 4,719,919 A | 1/1988 | Marchosky | |
| 4,987,896 A | 1/1991 | Nakamatsu | |
| 4,989,601 A | 2/1991 | Marchosky | |
| 5,314,458 A | 5/1994 | Najafi et al. | 607/116 |
| 5,471,991 A * | 12/1995 | Shinnar | 600/518 |
| 5,540,737 A | 7/1996 | Fenn | |
| 5,611,767 A | 3/1997 | Williams | |
| 5,713,923 A | 2/1998 | Ward et al. | 607/3 |

(Continued)

FOREIGN PATENT DOCUMENTS

WO WO 84/02839 8/1984

OTHER PUBLICATIONS

Callaghan, et al., "Cerebral Effects of Experimental Hypothermia", A.M.A. Archives of Surgery, 1954, 68, pp. 208-215.

(Continued)

*Primary Examiner*—Robert E. Pezzuto
*Assistant Examiner*—Frances P. Oropeza
(74) *Attorney, Agent, or Firm*—Pillsbury Winthrop Shaw Pittman LLP

(57) ABSTRACT

Analytical methods and devices for analyzing biological signals, for example, electrical signals from the brain to determine whether an abnormal condition caused by a medical condition exists. In one embodiment, the medical disorder may be epilepsy. The analytical methods include wavelet analysis and neighbor cross-correlation count, which is a frequency specific measure of the degree of correlation of a single channel of data with respect to its neighbors. The devices according to the invention are programmed to include the analytical methods and to administer treatment regimens such as electrical stimulation, heating, cooling and medication as needed.

11 Claims, 7 Drawing Sheets

U.S. PATENT DOCUMENTS

| | | | | |
|---|---|---|---|---|
| 5,716,377 | A | 2/1998 | Rise et al. | 607/2 |
| 5,735,814 | A | 4/1998 | Elsberry et al. | 604/43 |
| 5,782,798 | A | 7/1998 | Rise | 604/49 |
| 5,792,186 | A | 8/1998 | Rise | 607/2 |
| 5,916,242 | A | 6/1999 | Schwartz | |
| 5,925,070 | A | 7/1999 | King et al. | 607/67 |
| 5,938,689 | A | 8/1999 | Fischell et al. | 607/45 |
| 5,978,702 | A | 11/1999 | Ward et al. | 607/3 |
| 5,995,868 | A * | 11/1999 | Dorfmeister et al. | 600/544 |
| 6,016,449 | A | 1/2000 | Fischell et al. | 607/45 |

OTHER PUBLICATIONS

Wass, et al., "Hypothermia-associated Protection from Ischemic Brain Injury: Implications for Patient Management", pp. 95-111.

Frizzell, et al., "Effects of Etomidate and Hypothermia on Cerebral Metabolism and Blood Flow in a Canine Model of Hypoperfusion", Journal of Neurosurgical Anesthesiology, vol. 5, No. 2, pp. 104-110.

Koizumi, et al., "Effect of Hypothermia on Excitability of Spinal Neurons", Neurophysiol, vol. 23, 1960, pp. 421-431.

Tasaki, et al., "Action Currents of Single Nerve Fibers as Modified by Temperature Changes", Neurophysiol, vol. 11, 1948, pp. 311-315.

Fay, "Early Experiences with Local and Generalized Refrigeration of the Human Brain", Neurosurg, vol. 16, 1959, pp. 239-260.

Kawakami, et al., "The Influence of Temperature on the Balance Between the Excitatory and Inhibitory Cerebral Systems. A Contribution to the Caudate-Hypothalamic Antagonism", Electroenceph. Clin. Neurophysiol., 1963, 15: pp. 230-237.

Chatfield, et al., "The Effects of Temperature on the Spontaneous and Induced Electrical Activity in the Cerebral Cortex of the Golden Hamster", EEG Clin. Neurophysiol., 1951, 3: pp. 225-230.

Bindman, et al., "Comparison of the Effects on Electrocortical Activity of General Body Cooling and Local Cooling of the Surface of the Brain", Electroenceph. Clin. Neurophysiol. 1963, 15: pp. 238-245.

de Jong, et al., "Nerve Conduction Velocity During Hypothermia in Man", Anesthesiology, vol. 27, No. 6, Nov.-Dec. 1966, pp. 805-810.

Scott, et al., "The Effect of Lowered Body Temperature on the EEG", EEGJ, vol. 5, 1953, p. 465.

Jia, et al., "Cold Injury to Nerves is not Due to Ischaemia Alone", Brain (1998), 121, pp. 989-1001.

Michenfelder, "Barbiturates for Brain Resuscitation: Yes and No", Anesthesiology, vol. 57, No. 2, Aug. 1982, pp. 74-75.

Marion, et al., "The Use of Moderate Therapeutic Hypothermia for Patients with Severe Head Injuries: a Preliminary Report Report", J. Neurosurg 79: 1993, pp. 354-362.

Weinstein, et al., "Hypothermia and Electrical Activity of Cerebral Cortex", Archives of Neurology, vol. 4, Apr. 1961, pp. 441-448.

Hagerdal, et al., "Protective Effect of Combinations of Hypothermia and Barbiturates in Cerebral Hypoxia in the Rat", Anthesthesiology, vol. 49, No. 3, Sep. 1978, pp. 165-169.

Noell, et al., "Effects of Cold Exposure on Brain Activity", Federation Proceedings, vol. 11, p. 114.

Dietrich, et al., "Post-Traumatic Brain Hypothermia Reduces Histopathological Damage Following Concussive Brain Injury in the Rat", Acta Neuropathol (1994) 87: pp. 250-258.

Rosomoff, "Hypothermia and Cerebral Vascular Lesions", A.M.A. Archives of Neurology and Psychiatry, vol. 78, Nov. 1957, pp. 454-464.

Michenfelder, et al., "The Effects of Anesthesia and Hypothermia on Canine Cerebral ATP and Lactate during Anoxia Produced by Decapitation", Anesthesiology, Oct. 1970, vol. 33, No. 4, pp. 430-439.

Milde, et al., "Cerebral Functional, Metabolic, and Hemodynamic Effects of Etomidate in Dogs", Anesthesiology, vol. 63, No. 4, Oct. 1985, pp. 371-377.

Suda, et al., "Analysis of Effects of Hydrothermia on Central Nervous System Responses", Am. J. Physiol. 189(2) (1957); pp. 373-380.

Gaenshirt, et al., "The Electrocorticogram of the Cat's Brain at Temperatures Between 40° C., and 20° C.,", EEG Clin. Neurophysiol., 1954, 6: pp. 409-413.

Ommaya, et al., "Extravascular Local Cooling of the Brain in Man", J. Neurosurgery, vol. 20, 1963, pp. 8-20.

Berntman, et al., "Cerebral Protective Effect of Low-Grade Hypothermia", Anesthesiology, 55:, 1981, pp. 495-498.

Clifton, et al., "Marked Protection by Moderate Hypothermia After Experimental Traumatic Brain Injury", Journal of Cerebral Blood Flow and Metabolism, 11:, 1991, pp. 114-121.

Minamisawa, et al., "The Effect of Mild Hyperthermia and Hypothermia on Brain Damage Following 5, 10, and 15 Minutes of Forebrain Ischemia", Annals of Neurology, vol. 28, No. 1, Jul. 1990, pp. 26-33.

Marion, et al., "Treatment of Traumatic Brain Injury with Moderate Hypothermia", The New England Journal of Medicine, vol. 336, No. 8, Feb. 20, 1997, pp. 540-546.

Gunn, et al., "Selective Head Cooling in Newborn Infants After Perinatal Asphyxia: A Safety Study", Pediatrics, vol. 102, No. 4, Oct. 1998, pp. 885-892.

Pomeranz, et al., "The Effect of Resuscitative Moderate Hypothermia Following Epidural Brain Compression on Cerebral Damage in a Canine Outcome Model", J. Neurosurg. vol. 79, Aug. 1993, pp. 241-251.

Clasen, et al., "Hypothermia and Hypotension in Experimental Cerebral Edema", Arch Neurol., vol. 19, Nov. 1968, pp. 472-486.

Owens, "Effect of Hypothermla on Seizures Induced by Physical and Chemical Means", Am. J. Physiol. 193(3) (1958) pp. 560-562.

Marion, et al., "Treatment of Experimental Brain Injury with Moderate Hypothermia and 21-Aminosteroids", Journal of Neurotrauma, vol. 13, No. 3, 1996, pp. 139-147.

Busto, et al., "Small Differences in Intraischemic Brain Temperature Critically Determine the Extent of Ischemic Neuronal Injury", Journal of Cerebral Blood Flow and Metabolism, vol. 7, No. 6, 1987, pp. 729-738.

Denys, "AAEM Minimonograph #14: The Influence of Temperature in Clinical Neurophysiology", American Association of Electrodiagnostic Medicine, Sep. 1991, pp. 1-23.

Stevenson, et al., "Effects of Induced Hypothermia on Subcortical Evoked Potentials in the Cat", Am. J. Physiol. (194(2) (1958) pp. 423-426.

Scott, "EEG during Hypothermia", EEG Journal, vol. 7, 1995, p. 466.

Ferrari, et al., "Convulsive Electrocortical Discharges in Hypothermic Dog", EEG Journal, vol. 7, 1955, p. 441.

Marshall, et al., "Temporary Circulatory Occlusion to the Brain of the Hypothermic Dog", A.M.A. Archives of Surgery 72:, 1956, pp. 98-106.

Sedzimir, "Therapeutic Hypothermia in Cases of Head Injury", Journal of Neurosurg. vol. 16, 1959, pp. 407-414.

Frondel, "Reports", Science, vol. 124, Nov. 9, 1956, pp. 931-932.

Lee, et al., "Intraoperative Hippocampal Cooling and Wada Memory Testing in the Evaluation of Amnesia Risk Following Anterior Temporal Lobectomy" Arch Neurol, vol. 52, Sep. 1995, pp. 857-861.

Essman, et al., "Audiogenic Seizure in Genetically Susceptible Mice: Relation of Hypothermia to Onset and Susceptibility", Experimental Neurology, vol. 9, 1964, pp. 228-235.

Battista, "Effect of Cold on Cortical Potentials in the Cat", Experimetnal Neurology, vol. 19, 1967, pp. 140-155.

Vastola, et al., "Inhibition of Focal Seizures by Moderate Hypothermia ",Arch Neurol., vol. 20, Apr. 1969, pp. 430-439.

Lafferty, et al., "Cerebral Hypometabolism Obtained with Deep Pentobarbital Anesthesia and Hypothermia (30C)", Anesthesiology, vol. 49, No. 3, Sep. 1978, pp. 159-164.

Massopust, et al., "Cortical and Subcortical Responses to Hypothermia", Experimental Neurology, vol. 9, 1964, pp. 249-261.

Lipp, "Effect to Deep Hypothermia on the Electrical Activity of the Brain", Electroenceph. Clin. Neurophysiol., Vol. 17, 1964, pp. 46-51.

Swinyard, et al., "Effects of Alterations in Body Temperature on Properties of Convulsive Seizures in Rats", Amer. J Physiol., vol. 154, Aug. 1948, pp. 207-210.

Koella, et al., "The Influence of Temperature Changes on the Electrocortical Responses to Acoustic and Nociceptive Stimuli in the Cat", EEG Journal, vol. 6, 1954, pp. 629-634.

Nemoto, et al., "Suppression of Cerebral Metabolic rate for Oxygen ($CMRO_2$) by Mild Hypothermia Compared with Thiopental", Journal of Neurosurgical Anesthesiology, vol. 8, No. 1, 1966, pp. 52-59.

Botterell, et al., "Hypothermia in Neurosurgery", Part IV, pp. 363-368.

Meyer, et al., "Effects of Hypothermia on Local Blood Flow and Metabolism During Cerebral Ischemia and Hypoxia", J. Neurosurg., vol. 14, 1957, pp. 210-227.

Vacanti, et al., "Mild Hypothermia and Mg++ Protect Against Irreversible Damage During CNS Ischemia", Stroke, vol. 15, No. 4, 1984, pp. 695-698.

Smith, et al., "Mild Pre- and Posttraumatic Hypothermia Attenuates Blood-Brain Barrier Damage Following Controlled Cortical Impact Injury in the Rat", Journal of Neurotrauma, vol. 13, No. 1, 1996, pp. 1-9.

Young, et al., "The Effect of Graded Hypothermia on Hypoxic-Ischemic Brain Damage: A Neuropathologic Study in the Neonatal Rat", Stroke, vol. 14, No. 6, 1983, 929-934.

Buchan, et al., "Hypothermia But Not the N-Methyl-D-Aspartate Antagonist, MK-801, Attenuates Neuronal Damage in Gerbils Subjected to Transient Global Ischemia", The Journal of Neuroscience, 10(1), Jan. 1990, pp. 311-316.

Woodhall, et al., "The Physiologic and Pathologic Effects of Localized Cerebral Hypothermia", Annals of Surgery, vol. 147, No. 5, May 1958, pp. 673-683.

Mizuno-Matsumoto, Y., et al., "Visualization of Epileptogenic Phenomena Using Cross-Correlation Analysis: Localization of Epileptic Foci and Propagation of Epileptiform Discharges," *IEEE Transactions on Biomedical Engineering*, vol. 46, No. 3, Mar. 1999, pp. 271-279.

\* cited by examiner

SIGNAL ANALYSIS, HEAT FLOW MANAGEMENT, AND STIMULATION TECHNIQUES TO TREAT MEDICAL DISORDERS

CROSS-REFERENCE TO RELATED APPLICATIONS

This is a continuation-in-part of U.S. application Ser. No. 09/691,051, filed Oct. 19, 2000, now U.S. Pat. No. 6,882,881. which, in turn, claims priority to U.S. Provisional Application Nos. 60/160,328, filed Oct. 19, 1999, and 60/201,188 filed May 2, 2000. These applications are incorporated herein by reference in their entireties.

BACKGROUND OF THE INVENTION

1. Field of the Invention

The invention relates to methods for biomedical signal analysis, heat flow management, and stimulation techniques to treat medical disorders.

2. Description of Related Art

Biological signal processing and analysis can be used in a variety of contexts, ranging from purely scientific applications to patient diagnosis and treatment. Virtually any biological signal can be analyzed to yield scientifically or medically useful information, although bioelectrical signals, particularly from the nervous system, heart, and muscles, are very often analyzed in scientific and clinical contexts. During patient diagnosis and treatment, biological signal processing may be coupled to a treatment regimen, such as electrical stimulation or administration of medication.

Epilepsy is one example of a medical disorder in which bioelectrical signal processing and analysis has proven to be a useful part of a treatment regimen. In general, epileptic seizures occur because of an abnormal intensity and synchronized firing of brain cells. The fundamental neuronal disturbance during a seizure consists of large amplitude, sustained electrical depolarization, superimposed on which are a protracted volley of action potentials. The phenomena which cause these disturbances are not fully known at the time of writing. Generalized epileptic seizures may begin over the entire brain at essentially the same time, while more localized seizures, known as focal seizures, may begin in a more localized region in the brain and then spread.

Bioelectrical signal processing is used in the analysis and treatment of epilepsy to identify pre-ictal (i.e., pre-seizure), ictal, and post-ictal patterns from an electroencephalogram (EEG). When pre-ictal or ictal patterns are identified, a treatment regimen may be administered to the patient.

Two difficulties are often encountered in the kind of analysis-and-treatment scheme described above. The first difficulty lies in identifying the pre-ictal or ictal pattern so that a treatment can be administered. The second difficulty lies in synchronizing the application of the treatment regimen with the pre-ictal or ictal EEG signal so as to achieve maximum effect from the treatment.

Similar problems in identifying a desired portion of a biological signal and synchronizing treatment or analysis tasks with that desired portion of the biological signal occur in the analysis and treatment of many medical disorders.

SUMMARY OF THE INVENTION

One aspect of the invention relates to a method of analyzing a plurality of biological signals. The method comprises performing a wavelet transform on the plurality of biological signals. Thereafter, the method comprises, for at least one wavelet scale used in the wavelet transform, calculating the degree of correlation of each of the plurality of transformed biological signals with respect to at least one of the plurality of transformed biological signals, defining a correlation threshold, counting ones of the plurality of transformed biological signals having correlations to the at least one of the plurality of transformed biological signals that are greater than the correlation threshold, and comparing the results of the counting to a total number of possible correlations.

The method described above may be repeated for each wavelet scale used in the wavelet transform, in which case the total number of possible correlations may be the number of biological signals in the plurality of biological signals multiplied by the number of wavelet scales used in the wavelet transform. The wavelet analysis may be a discrete wavelet analysis.

In certain embodiments, the biological signals may be electrical signals from the nervous system or brain.

Another aspect of the invention relates to a method for treating a medical disorder. The method comprises performing a wavelet analysis on a plurality of biological signals from a patient to determine whether an abnormal state caused by the medical disorder is present. For at least one wavelet scale used in performing the wavelet transform, the method comprises performing a neighbor correlation count to determine whether a treatment regimen would ameliorate or terminate the abnormal state. If the abnormal state exists and the treatment regimen would ameliorate or terminate the abnormal state, the method further comprises administering the treatment regimen.

In certain embodiments, the medical disorder is epilepsy and the biological signals are electrical signals from the nervous system. Moreover, determining whether the treatment regimen would ameliorate or terminate the abnormal state may comprise determining whether the treatment regimen would ameliorate or terminate the abnormal state in a particular epoch of time.

These and other aspects, features and advantages of the invention will be described below.

BRIEF DESCRIPTION OF THE DRAWINGS

The invention will be described with respect to the following drawing figures, in which like numerals represent like features throughout, and in which.

DETAILED DESCRIPTION

Signal Analysis Methods

In general, the biological signal analysis methods according to the present invention may be used on bioelectrical signals, biochemical signals, and biological temperature signals/readings. The methods according to the present invention may be applied to a variety of tissues, organs, and organ systems, including the brain, central nervous system, heart, lungs, liver, spleen, stomach, gall bladder, pancreas, duodenum, intestines, endocrine organs, extremities, muscles and peripheral nerves. However, for convenience, certain portions of the following description will assume that the signal to be analyzed is a bioelectrical signal (for example, an EEG or portion thereof) from the brain.

Figure 1:
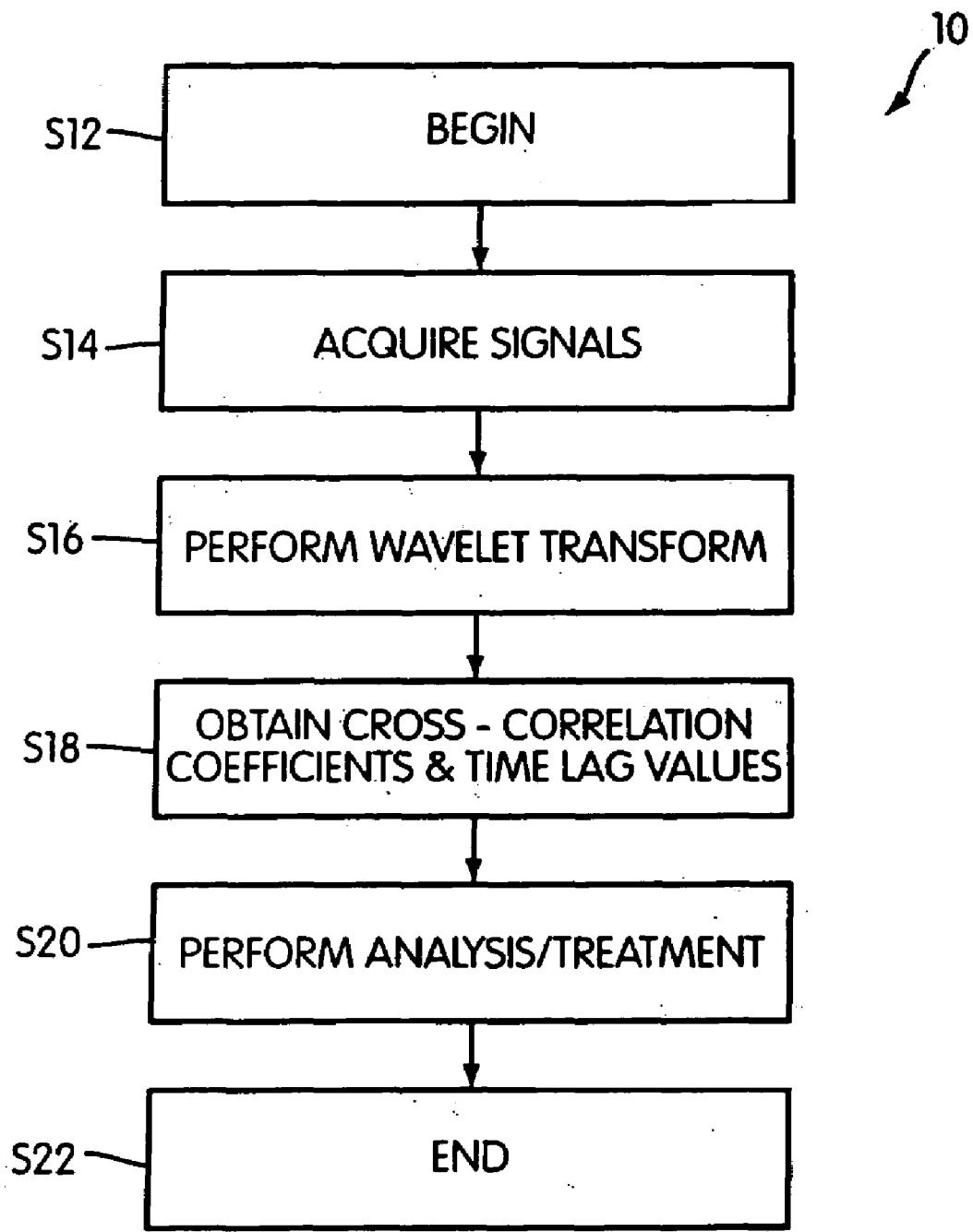
FIG. 1 is a high-level schematic flow diagram of a signal analysis method according to the invention.

FIG. 1 is a high-level schematic flow diagram of a biological signal analysis method 10 according to the present invention. In general, method 10 illustrates the basic tasks of a wavelet cross-correlation analysis. The method 10 begins in block S12, and continues at S14, in which one or more signals (e.g., indicating brain activity) are acquired from appropriate biological sensors, such as electrodes in electrical communication with the brain. Any number of electrodes may be used, depending only on the number of electrodes that are physically available and the number of electrodes that can be successfully monitored by the equipment used to monitor signals from those electrodes. If a single electrode is used, multiple sets of data may be gathered, and the remaining tasks of method 10 may be performed, by collecting data in different epochs of time. The electrodes may be placed either on or in the body, and may be connected to standard signal conditioning equipment to amplify the signals and to filter out unwanted noise and other non-biological artifacts.

Once the appropriate signals have been acquired from electrodes or other biological sensing elements, method 10 proceeds with task S16, in which wavelet transforms are computed for each signal. A wavelet transform provides information on the frequency content of the signal, as well as its characteristics in the time domain. Using the wavelet transform, higher frequency signals or portions of a signal are better resolved in time and low frequency signals are better resolved in frequency.

A wavelet transform of a signal is computed by projecting the signal onto a wavelet basis. In order to do so, a given basic wavelet g(t) is scaled by a in the time domain and is shifted by b repeatedly in order to generate a family of wavelets $g_{a,b}(t)$. The general continuous wavelet transform Wf(a,b) of a signal f(t) is calculated by applying equation (1):

$$Wf(a, b) = \int_{-\infty}^{\infty} \overline{g_{a,b}(t)} f(t) dt \tag{1}$$

in which f(t) is the signal, and $\overline{g_{a,b}(t)}$ is the conjugate complex of $g_{a,b}(t)$. The family of wavelets $g_{a,b}(t)$ is calculated given values of a, b, and t according to equation (2):

$$g_{a,b}(t) = \frac{1}{\sqrt{a}} g\left(\frac{t-b}{a}\right) \tag{2}$$

Many different basic wavelets are known and may be used as the "mother wavelet" g(t) in a wavelet transform according to the invention. However, the Gaussian wavelet, represented by equation (3) below, is one suitable wavelet function.

$$g(t) = e^{-\frac{t^2}{2}} \left( e^{j\Omega t} - e^{-\frac{\Omega^2}{2}} \right) \tag{3}$$

In equation (3), the constant $\Omega$ is chosen as $2\pi$. The Gaussian wavelet of equation (3) is suitable because the Gaussian function has least spread in domains of both time and frequency and the Gaussian wavelet is suitable for singularity detection in the form of non-orthogonal wavelets. Other wavelet functions, such as the Gabor function, may also be used.

As was explained above, equation (1) is the basic equation for the continuous wavelet transform. However, if method 10 is to be implemented numerically, for example, on a computer system connected to the electrodes, a discretized (sampled) version of the continuous wavelet transform or the discrete wavelet transform may be used. These discrete, numerical versions of the continuous wavelet transform are known those of ordinary skill in the art. An example of a discrete wavelet transform for numerical implementation will be given below in the examples.

As those of skill in the art will appreciate, in cases where a discrete wavelet transform is used, it is advantageous to select data points from the incoming signal to be sampled and/or transformed such that the individual data points provide as much useful biological information as possible while minimizing the time required to calculate the transform and the effort required to analyze the resulting data. For example, if a great number of data points are included in the wavelet transform, the resolution of the results may be adequate, but there may be too much data to analyze efficiently. In embodiments of the invention, discrete or sampled wavelet transforms would generally be performed such that at least three to four frequency scales are evaluated for each frequency octave, with more frequency scales evaluated in frequency octaves of particular interest. A frequency octave may be of particular interest if, for example, analytically relevant signal portions are known to occur in that particular frequency octave. The duration of each epoch of time in which data is evaluated (i.e., the epoch length) would also be chosen so as to produce a reasonable amount of data without losing biologically significant portions of the underlying signals.

Once the wavelet transform of the signal has been computed at S16, the signal is substantially stationary. Method 10 continues with task S18, in which wavelet cross-correlation coefficients (WCC) are obtained. The basic wavelet cross-correlation function is given below as equation (4):

$$WC_{x,y}(a, \tau) = \lim_{T \to \infty} \frac{1}{2T} \int_{-T}^{T} \overline{Wf_x(b, a)} Wf_y(b + \tau, a) db \tag{4}$$

in which $\tau$ is a time delay of wavelet coefficients in wavelet space. $WC_{x,y}(a,\tau)$ is complex-valued and consists of a real part $RWC_{x,y}(a,\tau)$ and an imaginary part $IWC_{x,y}(a,\tau)$. $RWC_{x,y}(a,\tau)$ can be used to express strength of correlation between two signals x and y. The wavelet cross-correlation coefficient $WR_{x,y}(a,\tau)$ (WCC) from the real part of wavelet cross-correlation function $RWC_{x,y}(a,\tau)$ is calculated using equation (5):

$$WR_{x,y}(a,\tau) = \frac{RWC_{x,y}(a,\tau)}{\sqrt{RWC_x(a,0)RWC_y(a,0)}}. \quad (5)$$

The time lag $\tau_{max\ x,y,a}$(TL) that gives maximum wavelet-crosscorrelation coefficient is calculated using equation (6):

$$\tau_{max\ x,y,a} = \arg\max WR_{x,y}(a,\tau), (-L_a \leq \tau \leq L_a) \quad (6)$$

in which $L_a$[msec] corresponds to the half-length of one wave for each scale, a. In task S18, the absolute value of the time lag (ATL) may also be calculated.

Once the WCC, TL, and ATL values have been calculated, task S18 is complete and method 10 continues with S20, an analysis or treatment task. The types of analysis and analysis-based treatment that may be performed vary and will be described in detail below with respect to the examples. For example, in the case of epilepsy, the wavelet cross-correlation performed in method 10 may be used to predict seizure onset, determine the optimal time to deliver treatment, and to determine the optimal method of delivering treatment. Method 10 ends at S22 in FIG. 1, although method 10 may be performed continuously or repeated as many times as desired. Moreover, in addition to the tasks shown in FIG. 1, method 10 may include conventional statistical analyses, such as alternating logistic regression (ALR), in order to aid the user in understanding the data developed using method 10.

Figure 2:
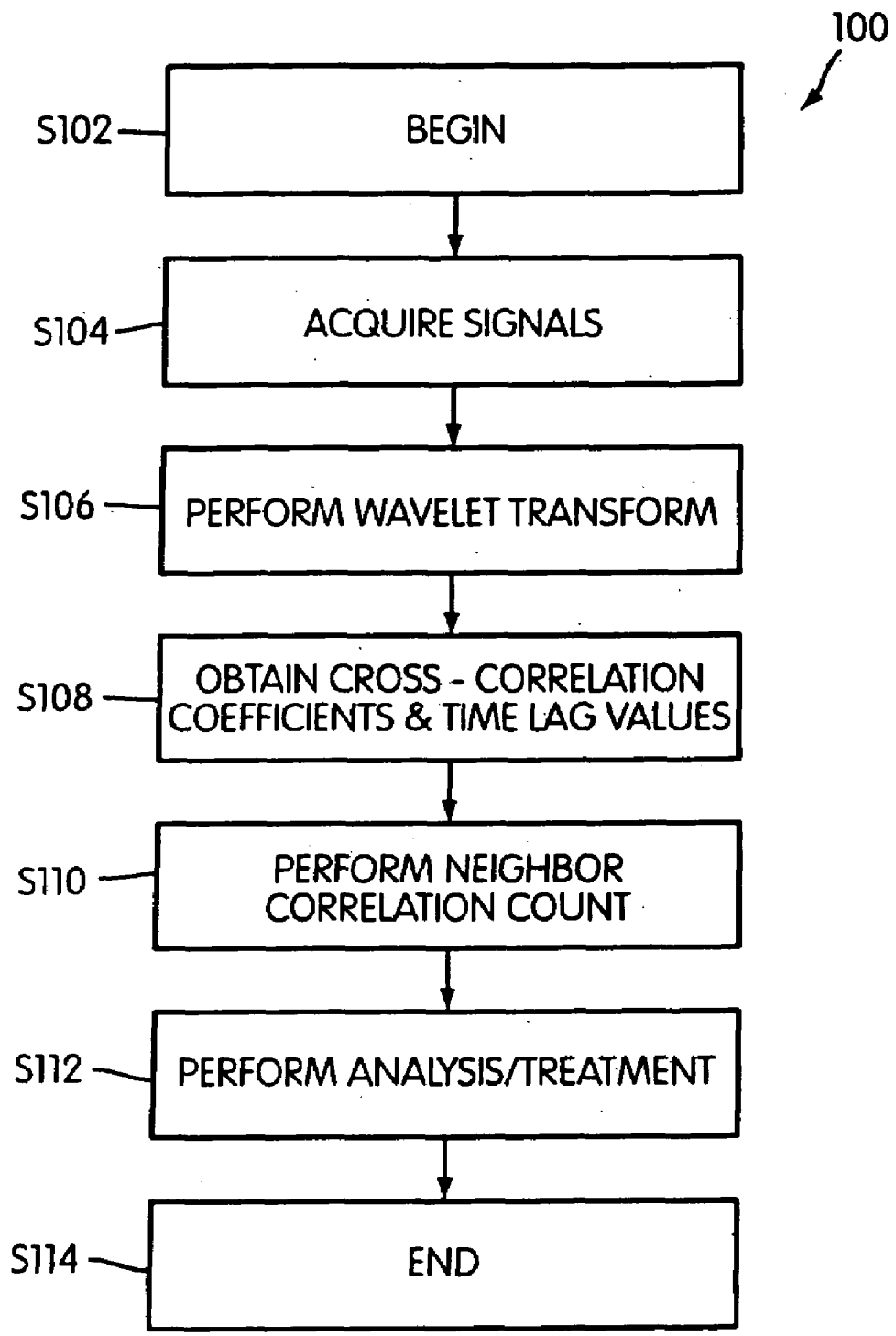
FIG. 2 is a high-level schematic flow diagram of another signal analysis method according to the invention.

FIG. 2 is a high-level schematic flow diagram of a method 100 according to the present invention. In a typical implementation of method 100, a number of data-gathering electrodes or other sensors would be used, each sensor gathering data in parallel with the others.

Method 100 begins at S102. Tasks S104, S106, and S108 of method 100 are substantially identical to tasks S14, S16 and S18 of method 10; therefore, the description above will suffice to describe them. Once task S108 is complete, method 100 continues with task S110.

In S110, a neighbor correlation count (NCC) is performed. NCC is a frequency-specific measure of the correlation of a single channel or sensor with respect to its environment (i.e., its neighbors). First, the WCC for a single channel with respect to each other channel or sensor is calculated for each wavelet scale that is used in the wavelet transform. Then, for the subject channel, the number of neighboring channels with WCCs that exceed a predetermined threshold for each scale is counted. That count is then typically expressed as a percentage of the maximum possible count for the given channel.

For example, in one two second epoch of time, if twenty channels of data are being recorded (each channel has 19 neighbors) and seven WCC scales are being measured, the maximum possible neighbor correlation count for each channel would be 133 (i.e., 19 channels multiplied by 7 wavelet scales). If 17 WCC measures are observed to be above a correlation threshold of, for example, 0.9, then the NCC would be 12.8%. Once the NCC has been calculated, it may be repeated for every channel in every epoch of time. NCC may be used as an indication of the degree of synchronization of a channel with its neighbors. As will be explained below with respect to the examples, by extension, NCC may also be used to determine whether a treatment regimen is likely to ameliorate or terminate an abnormal condition (e.g., an ictal or pre-ictal state) in a patient.

Method 100 continues with S112, an analysis or treatment task, before ending at S114. As with method 10, method 100 may be performed continuously, or repeatedly for different epochs of time.

Biological signal processing methods 10, 100 according to the invention may be implemented on a general purpose computer, a special purpose computing system, an ASIC, a digital signal processing (DSP) chip, or another known type of computing system. The number of channels or sensors that can be monitored and analyzed using methods 10, 100 according to the invention will vary according to the processing capabilities of the system on which the methods 10, 100 are implemented. The methods 10, 100 may be performed either in "real time" or once all data has been collected. If the methods 10, 100 are to be implemented in "real time" (i.e., wavelet transform/analysis occurs while data is being gathered and/or related treatments are being performed) using a system whose computing ability is limited, the methods 10, 100 may be limited to only a few channels, for example, four or five channels, each collecting data from a single sensor.

The following examples are illustrative of the use of the analysis methods according to the invention. In these examples, certain types of electrical stimulation will be described. These electrical stimulation methods, as well as other other treatment methods, will be described in further detail below.

EXAMPLE 1

Wavelet Cross-Correlation

Electrical stimulation of the brain is performed for a variety of clinical reasons, for example, to help localize areas of brain controlling movement, sensation, language, and other functions (sometimes referred to as "localizing stimulation" or LS). However, LS may produce activity of epileptiform morphology called afterdischarges. These afterdischarges can be understood as a model for epilepsy.

Afterdischarges and the effect of brief pulse stimulation (BPS) on afterdischarges were studied. No single, typical form of ADs was noted. Effect of BPS was not dependent upon pretreatment with anticonvulsant medication, relative time of ADs, or treatment latency. In addition, BPS was effective in all lobes stimulated, for all types of ADs, and both in regions that did and did not produce interictal epileptiform discharges; however, degree of effectiveness depended on these variables. For example, BPS was most effective anteriorly and least effective posteriorly. BPS were more likely to stop ADs if ADs consisted of continuous rhythmic epileptiform activity than to stop ADs that were rapidly repeated spikes. BPS of shorter durations (e.g., 0.5 to 1 second) were more effective than those of longer durations (e.g., 1.5 to 2 seconds). BPS was less effective if stimulation occurred at electrodes where interictal epileptiform discharges were found.

Wavelet cross-correlation analysis was used to obtain wavelet correlation coefficients (WCC), time lag (TL) and absolute values of TL (ATL) between two electrodes in accordance with method 10 described above. For Analysis-1, comparisons were made between WCC and ATL in epoch 1, which was prior to LS, epoch 2 which was after LS but before BPS, and epoch 3 which was after BPS. For Analysis-2, comparisons were made between WCC and ATL during four conditions during epoch 1. These were when BPS subsequently terminated ADs within two seconds (1A), terminated ADs within two to five seconds (1B) did not terminate ADs within five seconds (1C), and when ADs did not appear (1D). BPS efficacy in terminating ADs was predicted by (1) low correlation and (2) slow propagation speed between electrode pairs in 2–10 second period before stimulation. Therefore, wavelet cross-correlation analysis aids in predicting conditions during which BPS can abort ADs. When used according to the invention, similar analyses could help predict when BPS or other interventions would abort clinical seizures.

EXAMPLE 2

Wavelet Cross-Correlation

The value of wavelet cross-correlation analysis was assessed in 57 events in which afterdischarges (ADs) appeared in response to stimulation of brain cortical tissue in humans. Mean durations of epoch 1, 2 and 3 were 9.9, 11.3 and 14.5 seconds, respectively. For controls in analysis-2 we chose 59 events in which ADs did not appear after cortical stimulation. Significant differences of WCC values tended to occur between epochs 1 and 2, and 2 and 3. On the other hand, there were few significant differences in WCC between epochs 1 and 3.

The results suggested that activity propagated from one electrode to another with a time lag. Short time lags (less than 10 milliseconds) occurred less frequently during epoch 2, but that time lags of 10 milliseconds occurred more frequently during epoch 2.

In summary, results indicated that there were significant differences in WCC and TL when comparing among different epochs. These differences can be utilized to determine when seizures are likely to occur and to determine where they are originating and direction of propagation. The example pertains to results utilizing EEG analysis, but those skilled in the art will see that the methods of the invention could be utilized to analyze other data obtained from sensors placed on brain or elsewhere.

EXAMPLE 3

Discrete Wavelet Cross-Correlation/Neighbor Correlation Count

EEG Data were recorded from patients using Telefactor Beehives (Astro-Med, Grass-Telefactor, West Warwick, R.I., USA) sampling at 200 samples per second. The low pass filter was set at 70 Hz, while the high pass filter was set at 1 Hz. These systems use 12 bit analog to digital converters. The Beehives save recorded EEG data to a file server in data files. Those data files were analyzed off-line once data collection was complete.

In the analysis, which included the tasks of method 100, the discrete approximation to the continuous wavelet transform was used. The real part of the Gabor function, which is a cosine wave with an exponential taper, was chosen as the basic wavelet. The complex Gabor function was not used in order to simplify the calculations and increase processing speed. The use of only the real portion of the Gabor function did not result in any significant loss of information. The equation for the discrete wavelet transform with the Gabor wavelet function is given below as equation (7):

$$W_r(a, b) = \sum_{t=-L_w}^{t=+L_w} X(t) e^{-(t/a)^2} \left( \cos\left(\frac{2\pi(t-b)}{a}\right) - e^{-2\pi^2} \right) \quad (7)$$

in which:
  $W_r(a,b)$=real part of the discrete approximation for the continuous Gabor wavelet function;
  $X(t)$=EEG data samples;
  t=Sample index (time=t/sample rate in seconds);
  a=Frequency scale (Frequency of scale=sample rate/a);
  b=Wavelet position in samples with respect to EEG data samples; and
  $L_w$=2.2 periods of frequency scale a.

The Gabor function is of infinite length; however, the absolute value of the function approaches very small values after a few cycles of the base frequency. In the discrete approximation, therefore, it is only necessary to evaluate the sum in equation (7) over a few cycles of the base frequency, because larger summations consume more processor time but do not significantly change the numerical result. This saves considerable processor time, particularly for the higher frequency scales which have shorter periods compared to fixed length calculations. For this example, the wavelet function was evaluated over +/-$L_w$=2.2 cycles of the given scale, because the Gabor wavelet function is less than 1% of its maximum vale at that point.

Using the discrete wavelet transform, the degree of cross-correlation between channels is evaluated by applying equation (8):

$$WC_{rxy}(a, \tau) = \frac{\sum_{t=0}^{t=L_E} W_{rx}(a, t) W_{ry}(a, t-\tau)}{\sqrt{\sum_{t=0}^{t=L_E} W_{rx}(a,t)^2} \sqrt{\sum_{t=0}^{t=L_E} W_{ry}(a,t)^2}} \quad (8)$$

in which:
  $WC_{rxy}(a,\tau)$=Normalized Wavelet Cross Correlation between EEG channels X and Y, as a function of scale a, and time lag $\tau$. Range is −1.0 to +1.0;
  $L_E$=Epoch length of $W_{rx}$, $W_{ry}$. (i.e. 400 samples for 2 second epochs);
  t=Sample index; and
  $\tau$=Time lag between EEG channels X and Y.

At any given scale, the Gabor wavelet will produce a narrow band sinusoidal output. Correlating such signals can produce ambiguous maxima for absolute time lags greater than half a period of the given wavelet base frequency. For example, in the case of two pure sine waves of equal frequency, the cross-correlation is a sine wave of the same frequency, with a maxima occurring at every period of time delay shift. Accordingly, wavelet cross correlation is best evaluated for absolute time lags greater than half the period of the given scale at which the wavelet is being evaluated.

The discrete wavelet cross correlation (WCC) function $WC_{rxy}(a,\tau)$ was evaluated for two second, adjacent, non overlapping epochs for all channel pairs in the data set for a range of frequency scales. The epoch length was set at two seconds because that length represents a reasonable compromise between two competing advantages: longer epochs would improve the average estimate of WCC, but shorter epochs would be less likely to miss changes in WCC that result from the non stationary nature of the EEG.

The discrete values were chosen in a logarithmic fashion, so that at any given scale the interval (i.e., the increment to the next scale in the sequence) was a fixed proportion of the scale value itself. This arrangement gave constant proportional resolution in scale space. Each scale was chosen to be 7.18% higher the previous scale in the sequence. That provided 10 scale values in each octave (i.e., the scale value doubled every 10 steps). Seven scales in the frequency range 5 Hz to 8 Hz were used specifically: 7.69, 7.18, 6.70, 6.25, 5.83, 5.44 and 5.08 Hz. This range was chosen to cover the frequencies of ADs seen in earlier studies.

Wavelet cross-correlation can generate a large set of result data. For example, calculating only the maximum WCC (MaxWCC) for a single 2 second epoch of data from 20 channels of EEG using only 7 scales generates 1330 values (7 scales multiplied by 190 channel pairs). If the entire frequency range is used (i.e., 50 scales; 5 octaves at 10 scales per octave) then the number calculated values, 9500, exceeds the number of EEG data samples, 4000, by more than a factor of two. This is the classic "data explosion" problem; the goal of any analysis should be to reduce the number of data points to be reviewed, rather than increasing it.

One solution to the "data explosion" problem is to display the results graphically, but this may produce very complex displays, particularly if the graph is based on the original electrode positions. Another solution is to consider just the average of all the results, however some detail is lost using this solution. More information is preserved if a histogram of the MaxWCC values is used instead.

A histogram of MaxWCC values for all channel pairs for all selected scales in the study gives information about the group of electrodes as a single entity. The NCC measure described above provides information on the individual channels. For a given channel the number of correlation measures that exceed a predetermined threshold is counted. This count is taken for all neighbor channels and all scales selected for the study. The count is then expressed as percentage of maximum possible count for the given channel. In the case of one 2 second epoch, with seven WCC scales measured, the maximum count is 133=7×19.

EXAMPLE 4

Neighbor Correlation Count as an Indicator of Efficacy in Terminating Afterdischarges Electrical cortical stimulation was performed in six patients undergoing presurgical evaluations using subdural electrodes. The conditions altering BPS efficacy were evaluated in 272 electrodes showing ADs and 196 electrodes not showing ADs. Wavelet cross-correlation and neighbor correlation count methods similar to those of method 100 and Example 3 were used to evaluate the data for the two consecutive two-second time epochs before LS and after LS but before BPS. Additionally, alternating logistic regression (ALR) and generalized linear model (GLM) were used for statistical analysis.

The results demonstrated that BPS was more likely to stop ADs manifested by rhythmic pattern (type A) than those with rapidly repeating patterns (odds 2.4 times greater; p=0.002) or discrete individual spikes (5.3 times greater; p=0.148). BPS applied to an AD that had an absolute voltage that remained negative throughout the discharge was 13 times more likely to stop the AD when compared to BPS applied to an AD that was positive throughout, and BPS applied to an AD whose absolute voltage varied between negative and positive was 11 times more likely when compared to an AD that was positive throughout (p<0.001). BPS was also more effective when NCC values were higher, i.e., when ADs were more synchronized. Assessment of the 0–8 second period before LS showed that BPS efficacy improved by 8–11% per unit NCC increase during this period (p<0.001 to p=0.013).

Treatment Methods

Depending on the particular medical disorder that is to be treated, treatment methods and apparatuses according to the invention may involve administration of or be configured to administer electrical stimulation, heating, cooling, or medicament either singularly or in combination. Those treatments may be administered locally to any affected organ or organ system in the body, or they may be administered systemically. For example, in the case of epilepsy, electrical stimulation or medicament infusion may be applied to any brain area associated with seizures, including the neocortex, hippocampus, amygdala, thalamus, hypothalamus, caudate or other nuclei of basal ganglia, cerebellum, and brain stem. Treatment may be administered constantly, at fixed intervals, or as needed. Typically, treatments would be administered as part of a feedback loop in which a medical disorder is detected using methods 10, 100 according to the invention or other diagnostic sensing procedures and treatments are applied while the signals representative of the medical disorder (e.g., EEG signals) are monitored. In other embodiments, the physician or user may manually monitor the output of a method 10, 100 according to the invention and may decide when to begin and terminate treatment manually based on that output.

Electrodes used to provide electrical stimulation could be external electrodes placed on the skin, electrodes inserted percutaneously to a position under the skin, or electrodes that are implanted deep within the body, optionally along with a device to power and control the application of the electrical stimulation. (Examples of such implantable devices will be described below.)

Figure 3:
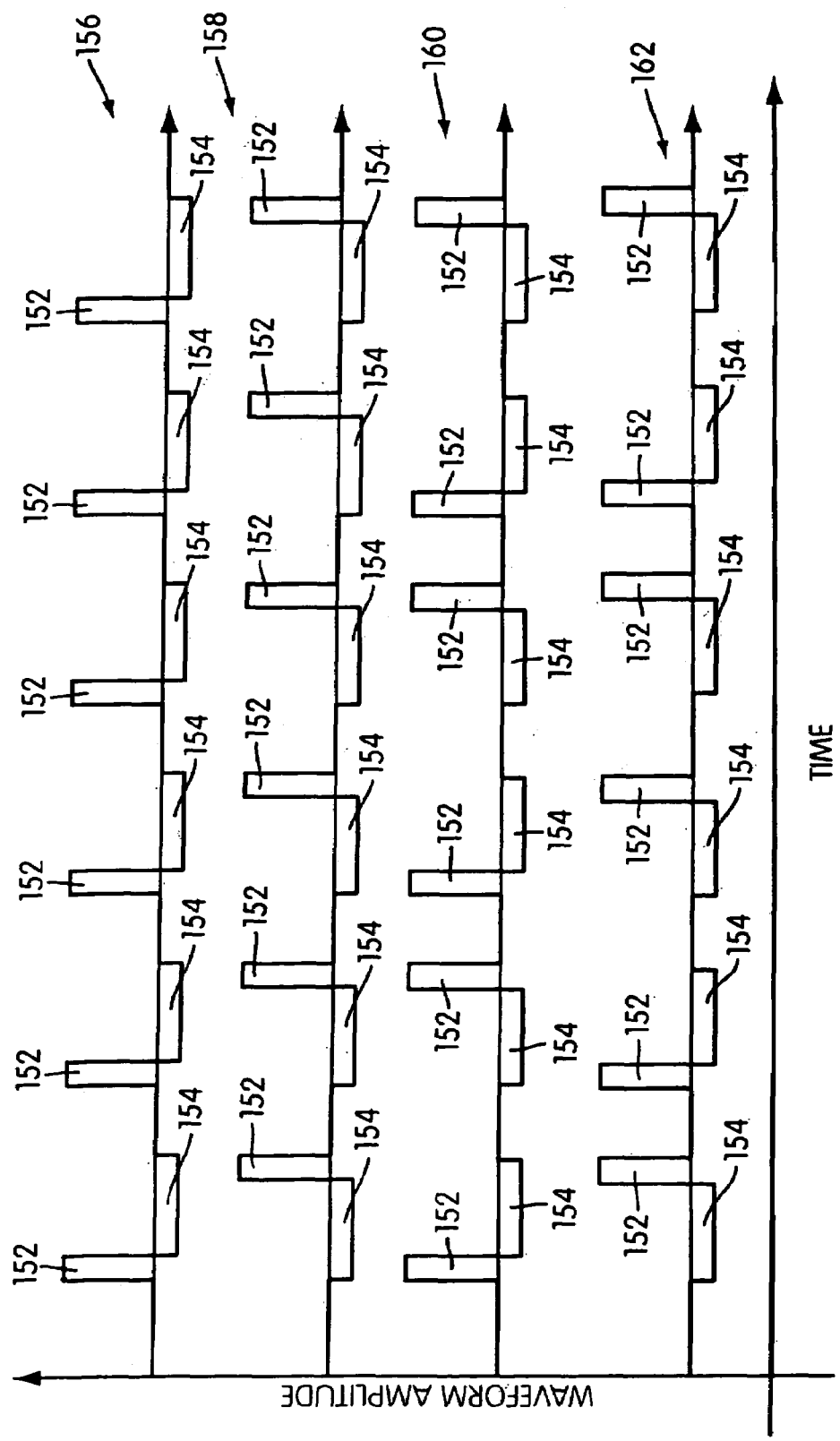
FIG. 3 is a waveform diagram illustrating several types of electrical stimulation waveforms that may be used in treatment methods according to the invention.

If electrical stimulation is applied, for example, near the focus of an epileptic seizure, it may be applied in the form of brief pulses, pulse trains, continuous waveforms, or some combination thereof, but is preferably applied in such a way as to preserve charge balance. Individual electrical pulses may vary in morphology, and may be symmetric or asymmetric. In particular, asymmetric biphasic pulses are suitable. FIG. 3 illustrates several types of electrical waveforms that may be used in electrical stimulation according to the invention. In FIG. 3, each of the waveforms includes active (positive voltage) pulses 152 and recovery (negative voltage) 154 pulses. Those pulses 152, 154 may be delivered in various sequences, including an active pulse 152 followed by a recovery pulse 154, as in waveform 156, a recovery pulse 154 followed by an active pulse 152, as in waveform 158, in alternating fashion, as in waveform 160, or randomly, as in waveform 162. Regardless of the type of waveform 156, 158, 160, 162, the integral with respect to time of the all the active pulses 152 minus the integral with respect to time of the recovery pulses 154 will always sum to zero, so that charge balance is maintained.

Medicament may be applied in any conventional manner, but depending on the implementation, it may be convenient or desirable to administer medicament by a catheter or other similar device placed directly in the affected tissues, organs, or organ systems. The particular medicaments, dosages, and infusion techniques can be easily determined by one of ordinary skill in the art depending on the condition to be treated and other conventional pharmacological and treatment considerations. In the case of epilepsy and other neurological disorders, representative examples of suitable medicaments include nucleic acids, hydantoins, deoxybarbituates, benzodiazepines, glutamate receptor agonists, glutamate receptor antagonists, γ-aminobutyric acid receptor agonists, γ-aminobutryic acid receptor antagonists, dopamine receptor agonists, dopamine receptor antagonists, anesthetics, electrolytes (e.g., sodium, potassium, and magnesium), and hormones. Other suitable medicaments include those affecting NMDA receptors, AMPA receptors, and metabotropic receptors.

Controlled warming and cooling may be applied as described in U.S. Pat. No. 6,248,126, the contents of which are incorporated by reference herein in their entirety. Warming and cooling may be applied to control swelling and inflammation, for example, swelling of brain or spinal tissue due to trauma, hemorrhage, encephalitis or myelitis. Mass lesions such as tumors, cysts, and abscesses may be reduced or eliminated by varying the temperature of the affected tissues. Moreover, intractable migraine headaches may also be controlled by controlling the temperature of the affected tissues.

Figure 4:
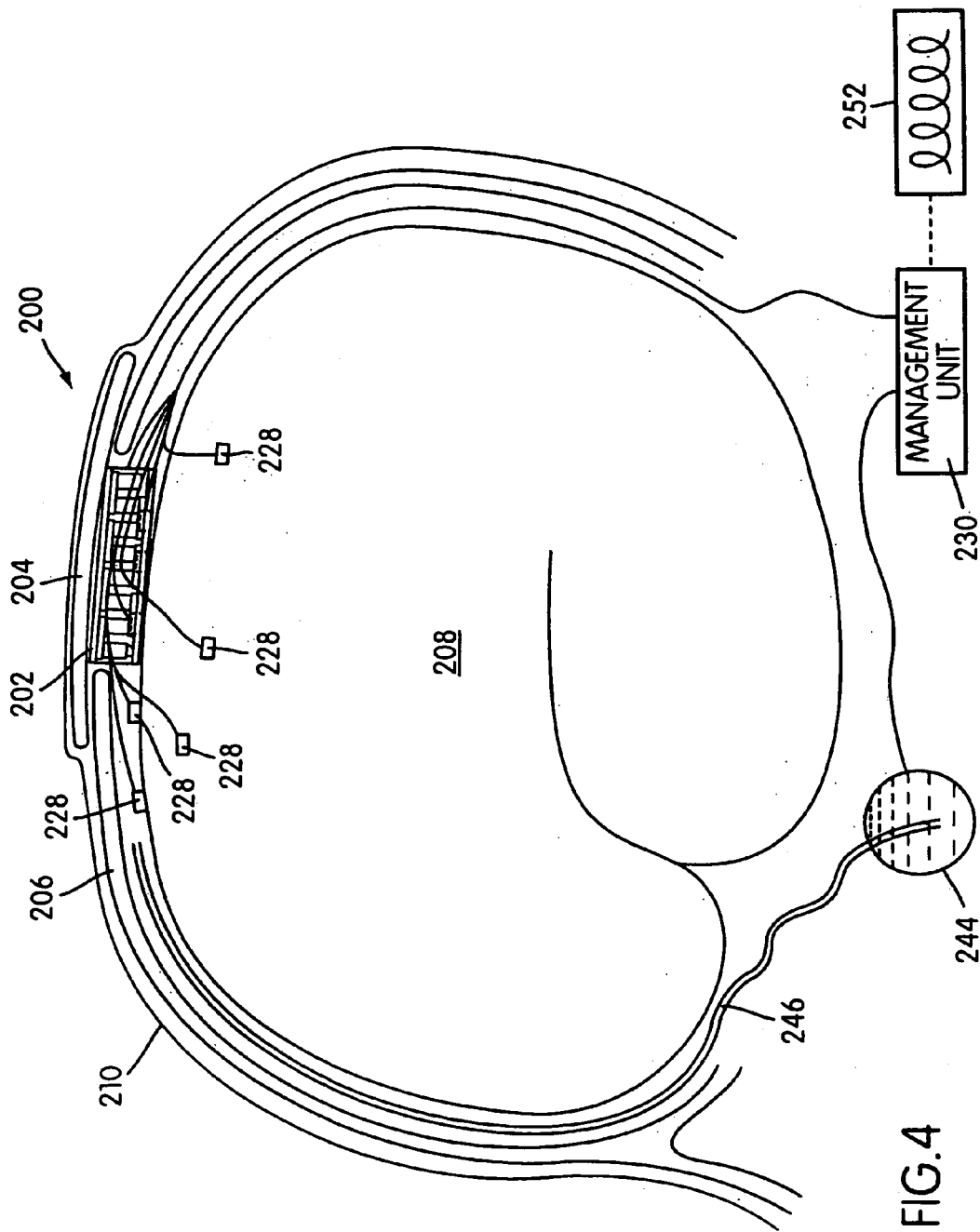
FIG. 4 is a schematic diagram of an implantable medical device according to the invention.

The methods 10, 100 according to the invention may be embodied or encoded in a variety of medical devices for patient treatment. FIG. 4 is a schematic view of an implantable device, generally indicated at 200, according to the invention. The device 200 is designed and adapted to provide medicament infusion, heating or cooling, and electrical stimulation in any combination, particularly to the brain and other central nervous system tissue.

The device 200 is an implantable device, although portions of it may be external to the body, as will be described below. In general, the device 200 comprises a sensor/effector component 202 in thermal communication with a heat sink 204, a management unit 230, and a refillable pump 244. The sensor/effector component 202 is implanted in a surgically-created opening in the skull 206 such that at least a portion of it is in direct contact with the brain 208; the heat sink 204 generally rests just beneath the scalp 210.

The heat sink 204 comprises a material of high thermal conductivity, for example, silicon oxide paste, encased in a thin, biocompatible membrane, such as silicone. While in thermal communication with the sensor/effector component 202, the heat sink 204 may be used to remove heat created by the normal operation of the sensor/effector component 202, so as to avoid tissue damage. The heat sink 204 may also be used to remove heat from the brain in cooperation with heat pumping components of the device 200 so as to cause tissue cooling.

In the embodiment illustrated in FIG. 4, sensor/effector component 202 comprises a set of upper and lower biocompatible substrates 212, 214. Each biocompatible substrate is formed of a material such as ceramic. However, the substrate may be made of substantially any biocompatible material, particularly those biocompatible materials having high heat conductivity. The two substrates 212, 214 vertically oppose one another. Between the two substrates 212, 214, a number of Peltier junction thermoelectric devices 216 are mounted.

Figure 5:
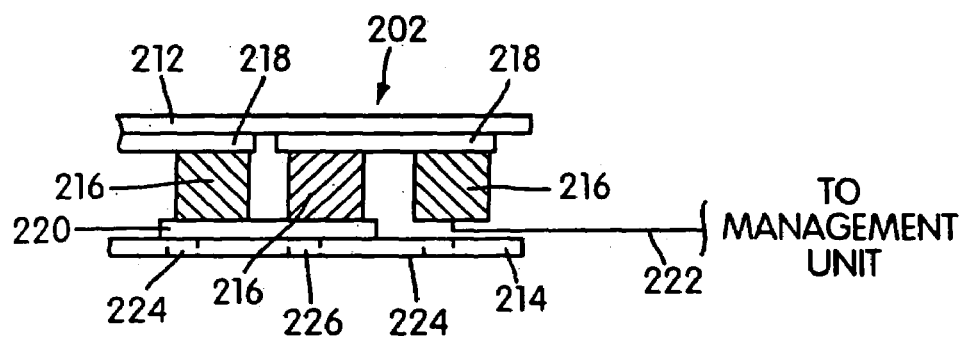
FIG. 5 is a schematic side elevational view of the sensor/effector component of the medical device of FIG. 4.

The arrangement of the two substrates 212, 214 with the thermoelectric devices 216 is shown in FIG. 5, a side elevational view of sensor/effector component 202. The thermoelectric devices 216 are connected in series by upper and lower junctions 218, 220. At respective ends of the series of thermoelectric devices 216, lead wires 222 are provided to connect the thermoelectric devices 216 to an appropriate power source (which will be described in more detail below). As used herein, the term "lead wire" may refer to a conventional wire, a microfabricated wire on a substrate, or any other form of connection that places one component in electrical communication with another.

Operationally, the direction of current flow through the thermoelectric devices 216 determines which of the upper and lower substrates 212, 214 is heated and which is cooled. As will be described in greater detail below, the power source for the thermoelectric devices 216 is adapted to The details of Peltier effect thermoelectric devices are well known to those of skill in the art and appropriate metals and junction characteristics can readily be selected by those of ordinary skill in the art so as to produce the desired magnitude of heating and cooling. Although shown schematically in the figures as being of relatively large size in relation to the substrates 212, 214, the size of the thermoelectric devices 216 may vary. The thermoelectric devices 216 may be fabricated by any conventional method, including microfabrication techniques.

Figure 6:
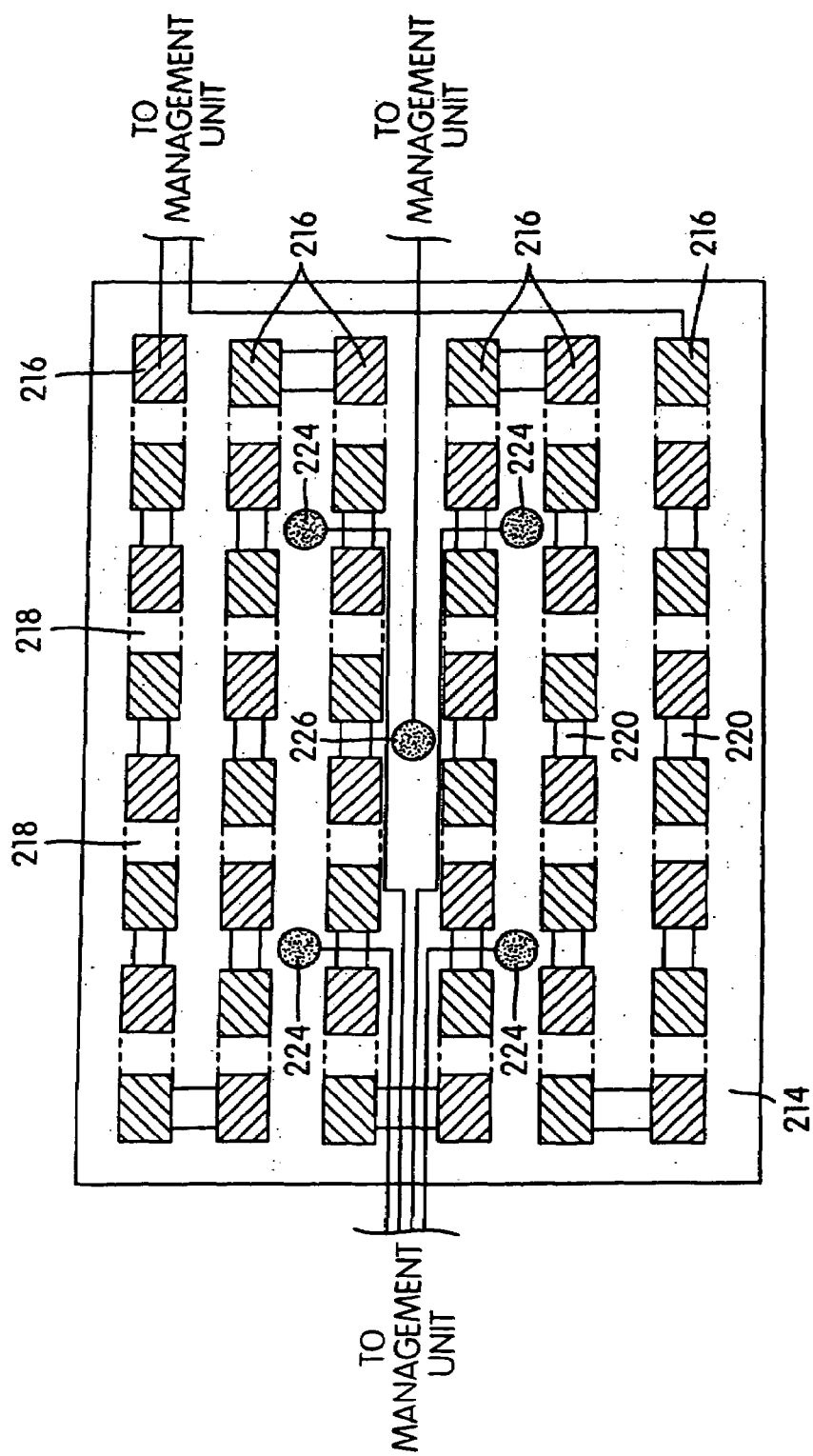
FIG. 6 is a schematic view of one substrate of the sensor/effector component of FIG. 5.

A number of sensors 224, 226 are provided on the lower substrate 214 so as to be in contact with brain tissue. FIG. 6 is a schematic view of sensor/effector component 202 with the upper substrate 212 removed so as to show certain features of the lower substrate 214, including its general layout. As shown in FIG. 6, the sensors 224, 226 are arranged on the lower substrate 214 and, in the illustrated embodiment, include dual purpose electrodes 224 that are configured and adapted to sense electrical activity and to deliver electrical stimulation. A biological temperature sensor 226 is also provided. Each of the sensors 224, 226 is connected to one or more lead wires 222.

The sensors 224, 226 may be mounted on the lower substrate 214 in a variety of ways. For example, if the sensors 224, 226 are provided as individual components, they could be seated and secured (e.g., by adhesives) in holes drilled through the thickness of the lower substrate 214, such that they are in contact with tissue. Alternatively, each of the sensors 224, 226 could be microfabricated on or attached to the underside of the lower substrate 214. If the sensors 224, 226 are provided as packaged chips, the lower substrate 224 may be provided with complimentary mounting structures appropriate for the chip packages. Depending on the type of sensor, one or more layers of insulation and/or passivation material may be provided between the sensor and the lower substrate 214. For example, thermal insulation may be provided between the lower substrate 214 and a biological temperature sensor 226 mounted on the lower substrate 214 to avoid obtaining erroneous readings.

As shown in FIG. 4, sensor/effector component 202 may also include one or more indwelling sensors 228 that are placed deep within the tissue and are connected either to the lower substrate 214 or to other components of the device 200 by lead wires 222. Such indwelling sensors are useful if an area deep within the tissue needs to be monitored, or if the desired biological signal cannot be gathered from a sensor 224, 226 mounted on the lower substrate 214. Indwelling sensors 228 would generally be placed in the desired locations by the surgeon during the placement procedure for the device 200.

Electrodes 224 and temperature sensors 226 were described above for purposes of illustration. However, substantially any type of sensor may be provided as a part of the device 200, including sensors that measure ionic concentration changes, cellular changes, blood flow changes, enzyme changes, hormonal changes, pH changes, changes in osmolality or osmolarity, cellular function, and optical changes. The data provided by the sensors 224, 226 may either be analyzed directly by a method like methods 10 and 100 as part of a protocol to determine whether a treatment regimen is necessary or would be effective, or they could be used for physiological "context," to be studied by a physician or researcher at a later date. Moreover, the indwelling sensors 228 could be any type of sensor described above, or any combination thereof. For example, a sensing/stimulating electrode could be packaged with a temperature sensor or pH sensor as one of the indwelling sensors 228.

The device 200 is managed by a management unit 230, to which the sensor/effector component 202 is connected. The management unit 230 is shown schematically in FIG. 7. As shown, the wire leads 222 from the various sensors 224, 226 connect first to amplifiers 232 which amplify the signals, and then to a digital-to-analog converter 233. From the digital-to-analog converter 233, the signals are sent to a microcontroller 234 (which may be a microprocessor, DSP chip, or ASIC) for analysis. The microcontroller 234 is coupled to memory 236 (which may be ROM, EPROM, EEPROM, or another similar type of memory) that includes instructions for performing an analysis method such as the methods 10, 100 that were described above. In addition to the analysis methods, the microcontroller 234 and/or its memory 236 includes instructions for effecting treatment protocols. The microcontroller 234 processes at least some of the signals provided to it to determine whether an abnormal state caused by a medical disorder exists (e.g., whether ictal or pre-ictal EEG patterns are present).

If an abnormal state does exist, the microcontroller 234 would implement one or more treatment protocols, either together or separately, to terminate or ameliorate the abnormal state. Such treatments would be timed or otherwise administered (e.g., using the results of a neighbor cross-correlation) so as to maximize their effect. For example, if electrical stimulation was required, the microcontroller 234 would actuate a stimulation switch 238, which would feed power to the electrodes 224. The management unit 230 also includes a second, separately controlled solid-state switch 240 to provide power to the thermoelectric devices 216, so that electrical stimulation and thermal treatments can be provided independently of one another.

Solid state switches are generally used for the switches 238, 240 because they are small, robust, have very low series resistance, and require very little electrical energy to operate. When applying stimulation current to electrodes, a solid state switch can switch rapidly (i.e., in less than a microsecond) so that the switch can produce the stimulation pulse train directly. The fast switching and very low series resistance of this type of switch means that variable pulse width modulation can be used to deliver continuous variable amounts of power to the various devices with virtually no energy or wasted heat being generated.

The microcontroller 234 would use a signal waveform such as a variable mark-space waveform to operate the switches 238, 240 so that one of the waveforms described above with respect to FIG. 3 is delivered. The microcontroller 234 is programmed to adjust the amplitude of each pulse so that charge balance is maintained.

The switches 238, 240 are connected to capacitors 242 or other conventional circuit elements in order to provide the correct voltages or other signal characteristics to the treatment devices. In particular, capacitors 242 ensure that there is no net charge imbalance during the period of stimulation for time spans that are long compared to the time constant of the capacitor and stimulation electrode 224 impedance combination. This time constant should be much longer than the pulse width in order to preserve original pulse shape. In other words, the charge balance afforded by the capacitors 242 is achieved at times longer than the time constant of the capacitor-electrode combination, which, in turn, is much longer than the widths of the stimulation pulses.

Figure 7:
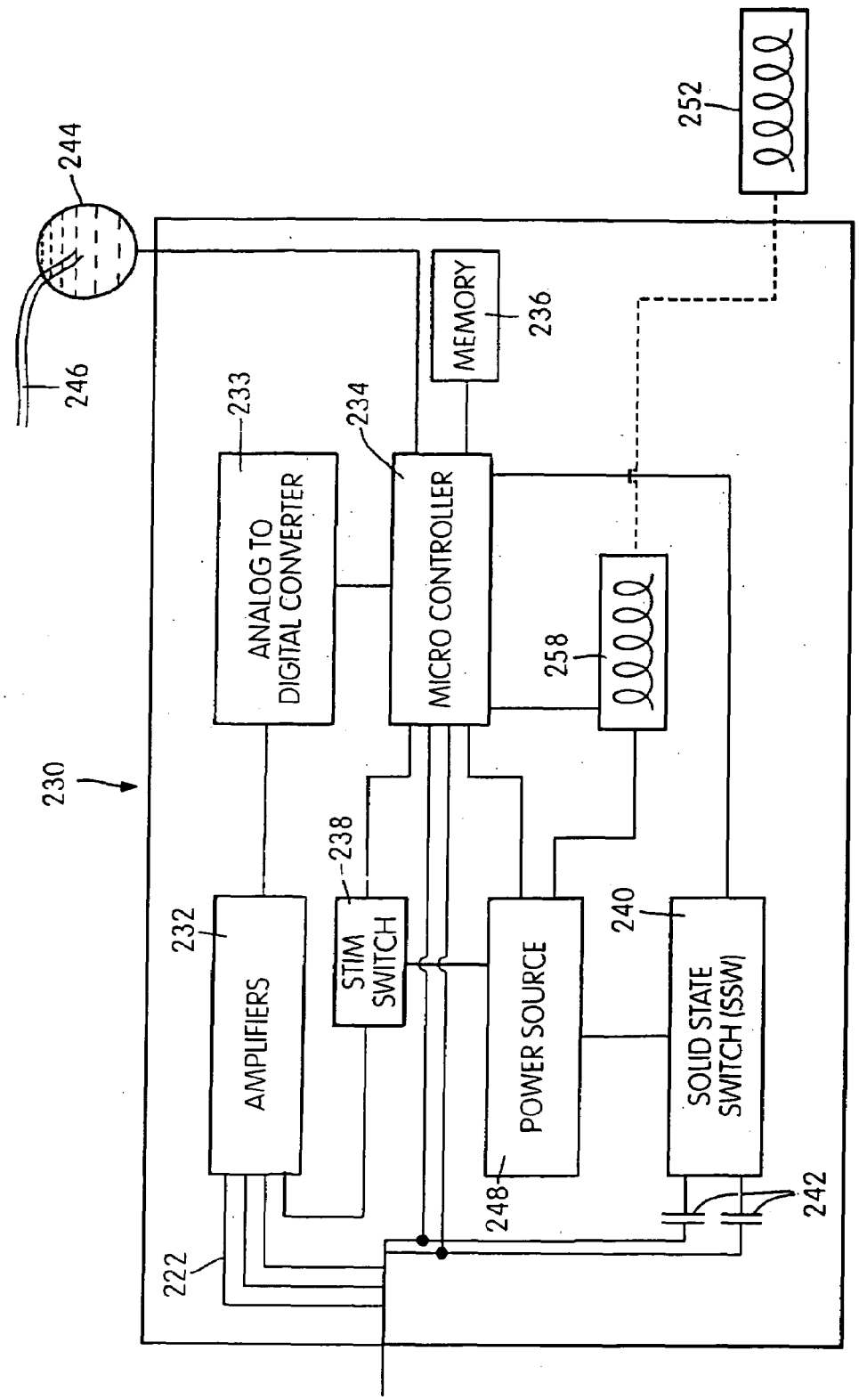
FIG. 7 is a schematic view of the components of the management unit of the medical device of FIG. 4.

The microcontroller 234 also controls a pump 244 that is constructed and adapted to cause medicaments to be administered to the patient through an appropriate catheter 246, as shown in FIGS. 4 and 7. Various types of implantable pumps with refillable reservoirs are known in the art and may be used as the pump 244. Alternatively, the pump 244 could be external to the body, with the catheter 246 inserted into an appropriate body tissue or body lumen for medicament delivery. The microcontroller 234 would activate the pump 244 if the results of a signal analysis showed that medicament administration was indicated.

The management unit 230 is powered by a conventional power source 248, which would typically be a conventional or rechargeable battery. The power source 248 is shown within the confines of the management unit 230 for ease of illustration; however, the power source 248 may be implanted in the body in a location separate from the management unit 230 and connected to the management unit 230. The power source 248 of the management unit 230 is coupled to an inductive loop power receiver 258 so that it may be recharged by an inductive power transfer device 252 positioned external to the body.

The following example is illustrative of certain treatment regimens according to the invention.

EXAMPLE 5

Cooling Neural Tissue

The effects of cooling neural tissue on seizure development were investigated using an EAAC1 knockout rat model of epilepsy. EACC1 antisense DNA was continuously infused into left ventricle of a test animal for 10 days using a pump located on animal's back. Diffuse glutamate toxicity was thereby effected in brain of knockout rat. Diffuse glutamate activity produced seizures, manifested by activity arrest, staring, and rhythmic 2–3/sec epileptiform EEG patterns, all indicative of seizure activity. Thereafter, test animal was anesthetized and a cooling unit adhered to rat's head. Due to thinness of rat crania, cooling of brain was achieved through intact rat skull. EEG tracings were made at baseline (28.8° C.) and at hypothermic (25.2° C.) temperatures. An overall reduction in seizure activity was observed after cooling, marked by return of normal exploratory behavior and normal EEG tracings.

Such temperature changes could be produced intracranially in other mammals by a device according to the invention, such as device 200.

While the invention has been described with respect to certain embodiments, those of ordinary skill in the art will realize that modifications and variations are possible within the scope of the following claims.

What is claimed is:

1. A method of analyzing a plurality of biological signals, comprising:
   performing a wavelet transform on the plurality of biological signals; and
   for at least one wavelet scale used in said performing:
      calculating a degree of cross-correlation of each of the plurality of transformed biological signals with respect to at least one of the plurality of transformed biological signals;
      defining a correlation threshold;
      counting ones of the plurality of transformed biological signals having correlations to the at least one of the plurality of transformed biological signals that are greater than the correlation threshold; and
      comparing the results of said counting to a total number of possible correlations.

2. The method of claim 1, further comprising repeating the method for each wavelet scale used in said performing.

3. The method of claim 1, wherein the biological signals are electrical signals from nervous system tissue.

4. The method of claim 3, wherein the electrical signals are from the brain.

5. The method of claim 2, wherein the wavelet transform is a discrete wavelet transform.

6. The method of claim 1, wherein a Gabor wavelet is used as a basic wavelet in performing the wavelet analysis.

7. The method of claim 1, wherein a Gaussian wavelet is used as a basic wavelet in performing the wavelet analysis.

8. The method of claim 2, wherein the total number of possible correlations comprises the number of biological signals in the plurality of biological signals multiplied by the number of wavelet scales used in said performing.

9. The method of claim 1, wherein calculating a degree of cross-correlation includes cross-correlating each of the plurality of transformed biological signals with respect to at least one of the plurality of transformed biological signals using a wavelet cross-correlation analysis.

10. The method of claim 1, wherein calculating a degree of cross-correlation includes calculating cross-correlation coefficients between each of the plurality of transformed biological signals and the at least one of the plurality of transformed biological signals.

11. The method of claim 1, the cross-correlation coefficients are calculated using a wavelet cross-correlation analysis.

* * * * *